(12) United States Patent
Song et al.

(10) Patent No.: US 6,435,001 B1
(45) Date of Patent: Aug. 20, 2002

(54) STEERING COLUMN IMPACT TEST PROCESS AND APPARATUS

(75) Inventors: Seung-Jae Song, Novi; Stephen P Gierak, Rochester Hills; Kenneth L Winalis, Mt. Clemens; Eugene M Schoenherr, Shelby Township, all of MI (US)

(73) Assignee: DaimlerChrysler Corporation, Auburn Hills, MI (US)

( * ) Notice: Subject to any disclaimer, the term of this patent is extended or adjusted under 35 U.S.C. 154(b) by 0 days.

(21) Appl. No.: 09/858,742

(22) Filed: May 16, 2001

(51) Int. Cl.[7] ................................................ G01M 7/00
(52) U.S. Cl. ..................................................... 73/12.04
(58) Field of Search ............................. 73/12.01, 12.04, 73/12.06, 12.07, 118.1, 865.3

(56) References Cited

U.S. PATENT DOCUMENTS 3,200,634 A * 8/1965 Rickards .................... 73/12.04
3,635,314 A * 1/1972 Mazelsky
5,861,544 A   1/1999 Kosaraju et al.
6,178,805 B1  1/2001 Kosaraju et al.

OTHER PUBLICATIONS

Federal Safety Standards MVSS 203 (five pages), Jun. 1984.
Steering Control System—Passenger Car—Laboratory Test Procedure—SAE J944, Jun. 1980 (three pages).

* cited by examiner

Primary Examiner—Robert Raevis
(74) Attorney, Agent, or Firm—Thomas A. Jurecko

(57) ABSTRACT

An apparatus and method for impact testing of vehicle components at a sub-system level includes a mobile unit and a vehicle sub-system. In an exemplary application, the vehicle sub-system includes a steering column and steering shaft. The vehicle steering column is securely mounted to the mobile unit and a mass element is secured to the steering shaft. By advancing the mobile unit into a rigid barrier at a predetermined speed, full-scale column collapse and energy absorption tests can be accurately analyzed at a significantly reduced cost and time.

7 Claims, 3 Drawing Sheets

STEERING COLUMN IMPACT TEST PROCESS AND APPARATUS

FIELD OF THE INVENTION

The present invention relates generally to a method and apparatus for testing a steering column assembly. More specifically, the present invention relates to an improved method and apparatus for testing the energy absorption of a steering column assembly in a simulated frontal crash.

BACKGROUND OF THE INVENTION

Many modifications aimed at increasing vehicle safety have been introduced over the years. In many cases these modifications were first introduced by one vehicle manufacturer, but were later required by law under the Federal Motor Vehicle Safety Standards (FMVSS) to improve vehicle safety. Currently, these standards apply to all vehicles sold in the United States.

There are three main categories of standards that apply to cars, those numbered in the 100's apply to crash avoidance, those numbered in the 200's apply to occupant protection, given that a crash occurs, and those numbered in the 300's apply to the immediate post crash considerations. The National Traffic and Motor Vehicle Safety Act of 1966 directed that all vehicles manufactured in 1968 or later satisfy a number of these standards; additional standards continue to be added.

The largest fatality reductions have been achieved from the combined effects of FMVSS 203 and FMVSS 204. FMVSS 203 requires energy absorbing steering columns to cushion the driver's chest impact in a frontal crash. FMVSS 204 requires limited rearward displacement of the steering wheel toward the driver. The present application is specifically concerned with testing of the FMVSS 203 standard.

FMVSS 203 the standard for energy absorbing steering columns is stated in 49 CFR 571.203. The standard requires the method of testing as described in SAE J944 JUN80 be followed to show compliance. In the J944 test, the steering column assembly instrumented with a 5-axis load cell, is mounted to a test fixture. A block of wood or other soft material, representing a human body, is discharged at a specific speed toward the steering column assembly. The contact of the block with the steering wheel element attached to the steering column produces an impact similar to a frontal crash. The energy absorption of the steering column is calculated using the data collected from the 5-axis load cell.

Although specific testing methods have been noted under the FMVSS 203, other testing methods have been developed to approximate the FMVSS tests while utilizing more efficient or reproducible tests. In particular a drop tower test has been developed to improve reproducibility. In the drop tower test, the steering column assembly is instrumented with a 5-axis load cell and a hemispherical element is mounted to the steering column shaft. The steering column assembly is mounted to the crosshead of a drop tower. The crosshead is raised to a height that will result in the assembly to obtaining a specified velocity at the point of impact. The contact of the hemispherical element attached to the steering column with the ground produces an impact similar to a frontal crash.

Although present testing methods have proven acceptable, each method has drawbacks. In tests where the column is impacted with another body, there are several concerns. First, the impact issuance of the allowed claims, and hereby preserve the right to again pursue the rejected claims in a continuation application.

Additionally, in the two testing methods described above, the energy absorbed by the steering column is calculated through the use of a 5-axis load sensor. These sensors, while commonly used, have inherent problems. First, the sensors separately measure components of force and components of moment. These components must then be combined to calculate the overall energy absorbed by the shaft using complex equations. Second, each load cell costs around $5000 each and are relatively fragile. Due to the dynamics of impact testing, the cells are often permanently damaged due to their fragility. As such, the cost of impact testing with 5-axis load sensors is high.

Next, the versatility of testing set-ups for the steering column assembly is also paramount. Since the steering column assembly is composed of several different sub-assemblies, each sub-assembly must be able to be tested individually. The present testing methods do not allow for simple conversions between testing set-ups for each of the sub-assemblies.

Another drawback to the present testing method is that impact testing does not allow high-speed cameras at any location around the steering column assembly. Unobstructed positioning of the camera allows capture of every part of the column as it collapses, providing more information on each test.

Lastly, another drawback of the current tests as described above is the correlation with actual vehicle tests. The tests as described above, do not resemble the Delta V, change in velocity, pulse of an actual vehicle crash test. In an actual vehicle crash test the Delta V pulse resembles a sinusoidal shape. In the current tests, the Delta V pulse has a triangular shape with very steep deceleration.

While many attempts have been made to develop a method and apparatus to test the amount of energy absorbed by a steering column, the variations in test accuracy, test repeatability, test versatility, test correlation, data acquisition and camera coverage have exposed the limitations of each known design. Thus, it remains desirable in the art to provide a method and apparatus of testing which overcomes all of these limitations.

SUMMARY OF THE INVENTION

It is a general object of the present invention to provide an improved method and apparatus for testing automobile components wherein the energy absorbed by the component is obtained through the rapid deceleration of the component having a mass element attached to one end.

It is another object of the present invention to provide an improved method and apparatus for testing the energy absorbed by an automobile steering column. The method including the steps of mounting the steering column to a fixture, attaching a mass element to the shaft of the steering column and rapidly decelerating the fixture to approximate a frontal crash.

In one form, the present invention provides an improved method and apparatus of testing the energy absorbed by an automobile steering column in a frontal crash. The method including the steps of mounting the steering column assembly to a fixture, attaching a mass element to an end of the steering column assembly, accelerating the fixture at a specified rate and determining the force produced on the steering column assembly at specified times.

Additional benefits and advantages of the present invention will become apparent to those skilled in the art to which this invention relates from a reading of the subsequent description of the preferred embodiment and the appended claims, taken in conjunction with the accompanying drawings.

DETAILED DESCRIPTION OF THE PREFERRED EMBODIMENT

Figure 1:
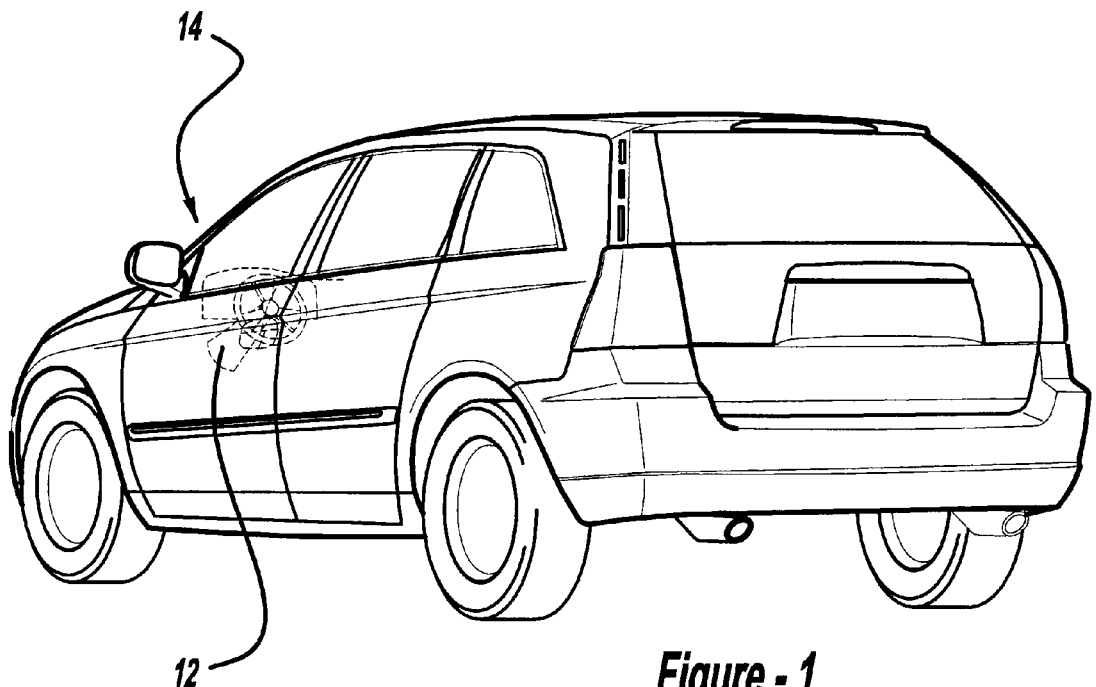
FIG. 1 is a perspective view of a steering column sub-system of a motor vehicle to be tested through application of the method of the present invention shown incorporated into a motor vehicle, the remainder of the vehicle shown in phantom lines.

Turning to FIGS. 1–4 of the drawings, an arrangement for testing the crashworthiness of motor vehicles sub-systems is generally identified in the drawings with reference numeral 10. The testing arrangement 10 is shown through the drawings specifically adapted for impact testing of a steering column 12. However, as will become apparent below, the teachings of the present invention are more broadly applicable to impact testing for various sub-assemblies or components of a motor vehicle.

Figure 2:
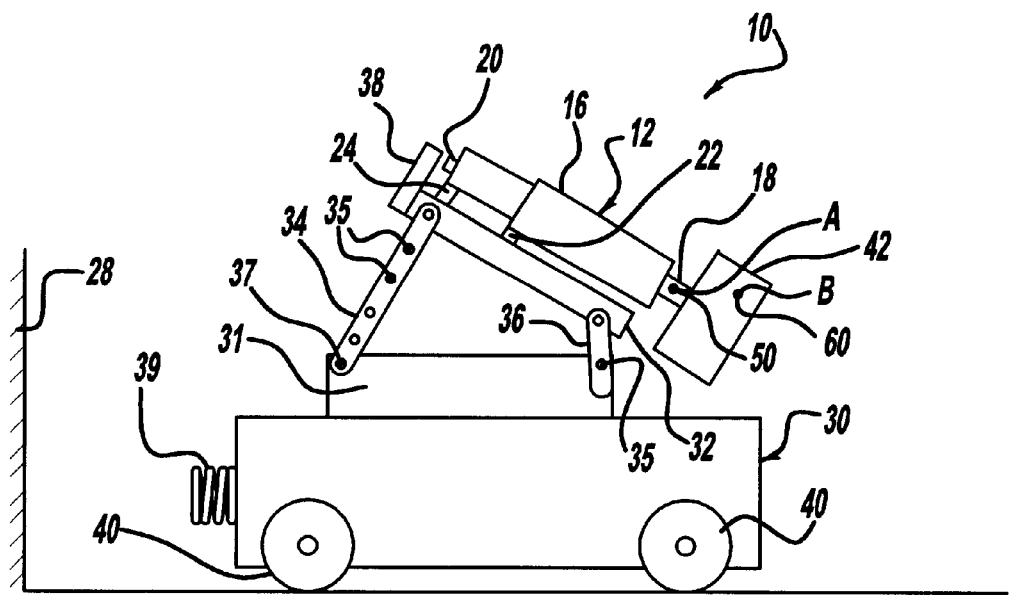
FIG. 2 is a side view of an impact testing arrangement constructed in accordance with the teachings of a preferred embodiment of the present invention illustrating the vehicle sub-system mounted to a cart.

As best shown in FIG. 2, the preferred testing arrangement 10 includes a mass element 42 mounted to the main shaft of steering column 12 which is securely mounted to a cart 30. The cart 30 is impacted with a rigid barrier 28 to simulate a frontal crash.

FIG. 1 illustrates the steering column 12 positioned within a motor vehicle 14 (otherwise shown in phantom). The steering column 12 includes a column housing 16, a main shaft 18, an intermediate shaft 20, a main support 22 and a secondary support 24.

Among the various tests which are conducted on motor vehicles is a steering column impact test in which a projectile block is impacted with the steering column assembly at a pre-determined speed. The steering column is placed to approximate a frontal collision. Impact testing is conducted to assess steering column collapse and energy absorption, among other items. It is this particular test for which testing arrangement 10 of the present invention is specifically designed to test the steering column in an isolated state, i.e. without the steering wheel and airbag. However, the teachings of the present invention are applicable to other types of crashworthiness testing.

Figure 3:
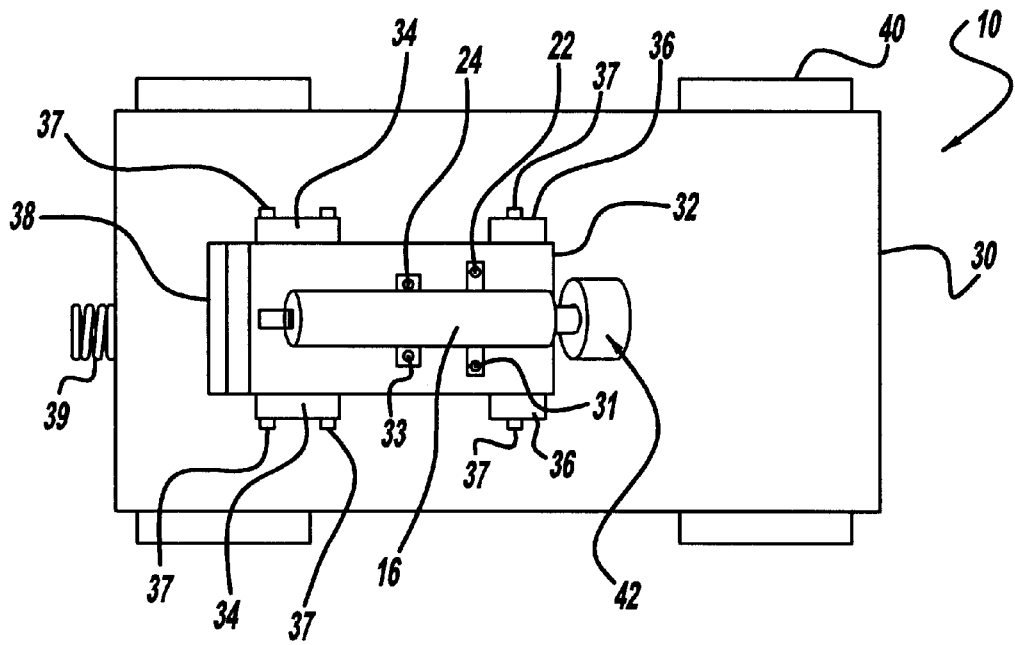
FIG. 3 is a top view of the impact testing arrangement of FIG. 2.
Figure 4:
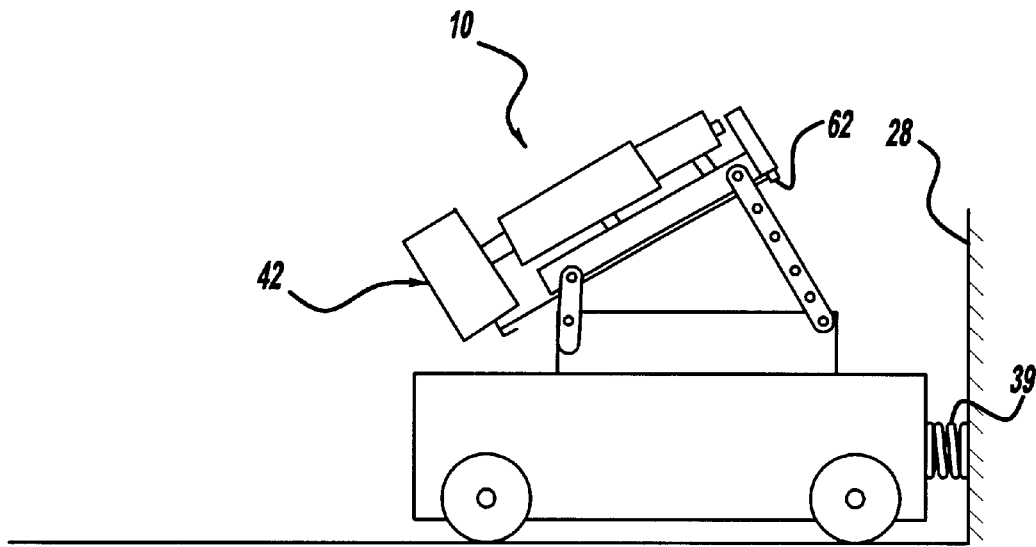
FIG. 4 is a right side view of the testing arrangement of FIG. 2 shown with a rigid impact barrier immediately prior to impact therebetween.

With continued reference to FIGS. 2–4, the testing arrangement of the preferred embodiment of the present invention will now be further discussed. Steering column 12 is shown most clearly in the top view of FIG. 3 removably attached to fixture 32. Fixture 32 is defined by a generally rectangular body having a plurality of holes drilled therethrough at locations according to the fastener holes on supports 22 and 24 of steering column 12. It is a preferred construction of the present arrangement that fasteners common to the vehicle assembly process be used to attach steering column 12 to fixture 32. However, it is understood that other means of fastening may be used to releasably attach steering column 12 to fixture 32. Fixture 32 is adjustably mounted to base 31 through adjustable link 34 and link 36. Link 36 is a generally elongated member having two mounting holes 35 located at opposite ends. Inserted through mounting holes 35 are fasteners 37 for attaching link 36 to base 31 and fixture 32. Similarly, adjustable link 34 is also a generally elongated member for attaching the opposite ends of fixture 32 and base 31 together. In a preferred embodiment, link 34 is significantly longer than link 36 and contains a plurality of mounting holes 35. Mounting holes 35 can be selectively used to attach fixture 32 to base 31 at multiple different angles. The alternate positioning of fixture 32 allows steering column 12 to be orientated similar to the variable positions experienced in the vehicle (e.g. the tilt position of the steering column). It can also be appreciated that the length of links 34 and 36 as well as the location of mounting holes 35 may be changed to achieve different positioning and angles of fixture 32.

Base 31 is mounted on cart 30 as best shown in FIG. 2. During the impact test, cart 30 is impacted with a rigid barrier 28. The cart 30 is illustrated to include a plurality of wheels 40. The weight and velocity of cart 30, among other factors, are chosen such that impact testing of steering column 12 is representative of full-scale impact testing.

In order to approximate impact with an occupant chest, testing arrangement 10 utilizes a mass element 42. Mass element 42 having a generally cylindrical shape is attached to main shaft 18 of steering column 12. In the preferred embodiment, mass element 42 has a weight of approximately 60 pounds. As described above, cart 30 is impacted with rigid barrier 28 to approximate a frontal crash. In this impact, the cart 30 slows and creates a deceleration pulse. Mass element 42 experiencing the deceleration of the attached cart applies an inertial force directly onto steering column 12. The intensity and magnitude of the inertia force can be controlled by various factors such as the weight of the mass element 42, cart velocity and deceleration intensity.

The calculation of the forces on steering column 12, can be accomplished by two separate modes. In a first mode, a five-axis load cell 50 (best shown in FIG. 2) is mounted around main shaft 18 of the steering column at point A to capture moments and forces. Upon impact with rigid barrier 28 the inertial forces of mass element 42 are transferred to main shaft 18. Five axis load cell 50 sends electrical signals representing the magnitude of each force and moment on the shaft to a microprocessor or other storage device. These signals are compiled and used to calculate the energy absorbed by the steering column 12 during the- impact. In a second mode, an accelerometer 60 is mounted to mass element 42 at point B. Upon impact, the mass element 42 is rapidly decelerated. Accelerometer 60 sends an electrical signal representing the magnitude of the acceleration to a microprocessor or other storage device. This signal is combined with the known mass of mass element 42 in a simple force/mass equation (F=m a) to compute the forces and energy on steering column 12 during the impact.

In a second embodiment of the present application, testing arrangement 10 utilizes a spring 39, or any cushion material (such as rubber blocks), attached to the front of cart 30 for changing the acceleration pulse of the cart 30. As cart 30 approaches impact with rigid barrier 28, spring 39 is compressed and provides a force that opposes the velocity vector of the cart. As such, the cart begins to slow down prior to impact with rigid barrier 28. The resultant acceleration pulse, like a full-scale impact acceleration pulse, resembles a sinusoidal shape.

In a third embodiment of the present application, testing arrangement 10 utilizes a blocker 38 as shown in FIG. 2 to test the collapsibility of intermediate shaft 20. Blocker 38, constructed of a high strength material such as steel, is attached to fixture 32 adjacent to intermediate shaft 20. In the impact test described above, the mass element 42 collapses the column. Blocker 38 prevents forward travel of the intermediate and main shafts causing the inertia force of the mass element to be completely absorbed by shafts 18 and 20. As shown in FIG. 4, a string potentiometer 62 is attached to mass element 42 and the underside of fixture 32. String potentiometer 62 measures the relative displacement of mass element 42 to determine the overall collapse of the column.

Figure 5:
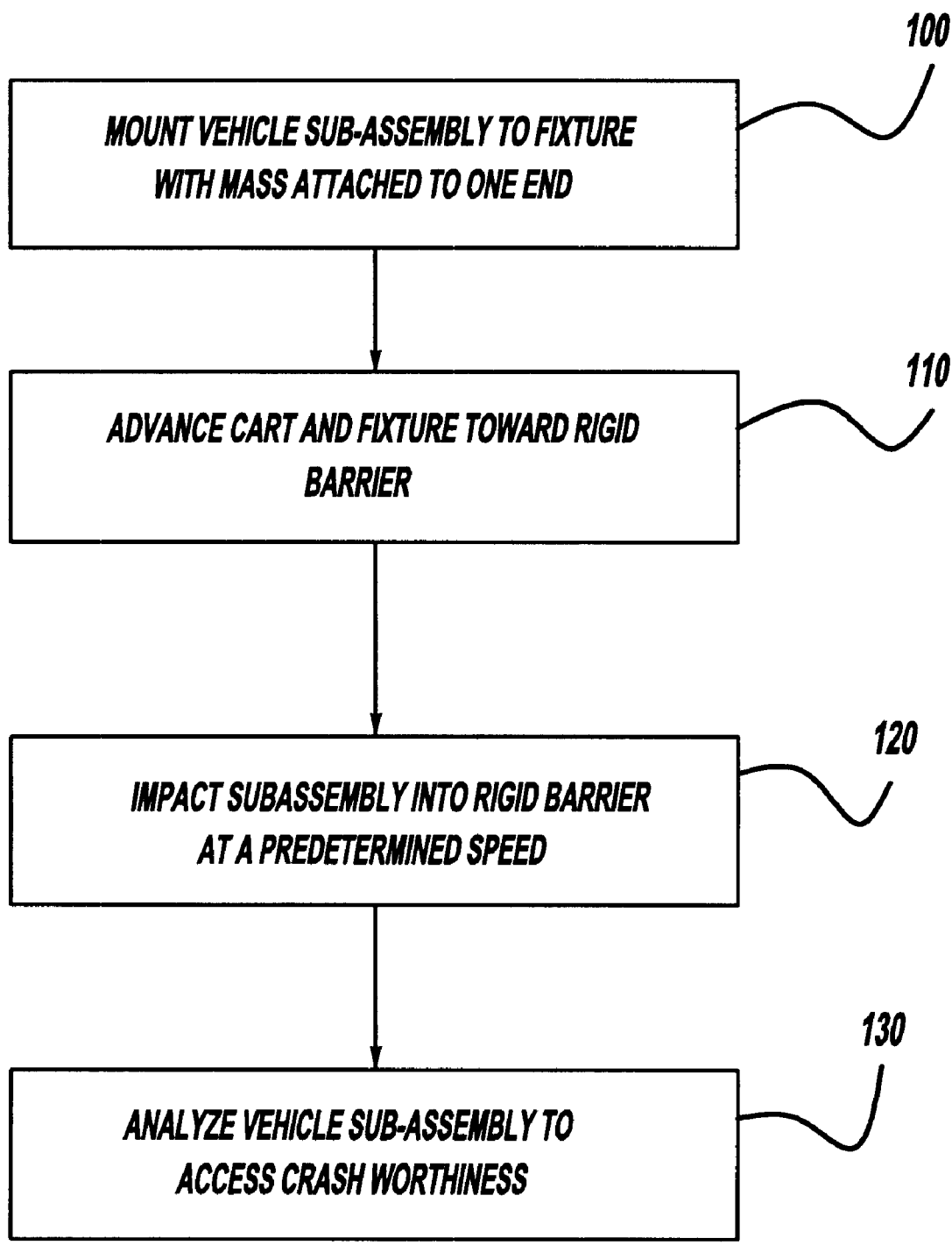
FIG. 5 is a flow diagram illustrating the general steps of the preferred method of the present invention.

With continued reference to FIGS. 1–4 and additional reference to the flow diagram of FIG. 5, the preferred method of the present invention will be described. The first general step 100 of the method involves mounting the vehicle steering column 12 to fixture 32. As noted above, steering column 12 is bolted or otherwise attached to fixture 32.

The next general step 110 of the method of the present invention involves advancing cart 30 toward rigid barrier 28. As shown in FIG. 4, cart 30 is preferably oriented to ensure the spring 39 encounters the rigid barrier 28 first, followed by the cart 30. This configuration ensures a sinusoidal energy impulse caused by the impact forces to more closely approximate a full-scale impact situation.

The next general step 120 of the preferred method of the present invention involves impacting the cart 30 into the rigid barrier 28 at a predetermined speed. In one particular application, cart 30 is impacted with rigid barrier 28 at a speed of approximately fifteen miles per hour. However, it will be appreciated by those skilled in the art that the speed of impact may be adjusted depending on factors, including but not limited to, the combined weight of the mass element 42 and the deceleration impulse.

The final general step 130 of the present invention involves analyzing steering column 12 to assess energy absorption of the column assembly. The steering column collapse and energy absorbed calculated through impact testing of the steering column 12 as described, is indicative of full-scale impact testing. Upon analyzing the testing results, subsequent design iterations of the components included within the steering column 12 may be made to improve the crashworthiness of the steering column 12 (i.e. to reduce the forces transferred to the driver from the steering column).

The general advantages of the present method over prior methods as described above improve variations in accuracy, test repeatability, test versatility, test correlation, data acquisition and camera coverage.

The present method increases the accuracy over prior methods by eliminating the frictional forces associated with impact testing. The body causing the deformation, the mass element in the present application, unlike the prior test methods is always connected to the steering column, thus eliminating any frictional loss associated with impacting the steering column.

The present method increases the test repeatability over prior test methods by eliminating variations in contact with the steering column. The present method unlike other methods does not use projectile bodies to simulate steering column impact during a frontal crash. The use of projectile objects may lead to variations in impact position and impact angle. The mass element of the present application has minimal variation in position and angle in attaching to the shaft, thus improving repeatability of the test.

The arrangement of the present testing apparatus and method are not restricted to testing the energy absorption of the steering column. Additional components of the steering assembly can also be tested using the present invention. In a second test, releasable fasteners (e.g. shear capsules) which releasably connect the steering column to the vehicle may be tested. The inertial forces of the mass element are applied to the shear capsules, providing qualitative results. In a third test, the steering column with mass element attached are mounted to the test apparatus with a lower rigid mounting bracket at the base of the column and releasable fasteners in the other mounting positions. The column as described above, is impacted into a rigid barrier. The inertial force from the mass element causes releasable fasteners to shear while the rigid mounting bracket retains the base of the column. The test determines the collapse of the column assembly. In a third test, the tilt mechanism is tested. The steering column assembly is securely mounted to the testing apparatus at a specified angle. The test apparatus allows for quantitative measurement of the resistance forces of anti-ratcheting of the tilt mechanism on the column.

Additionally, the present method has improved correlation to full vehicle impact tests. Spring 39 impacts barrier 28 directly before cart 30. The spring impact simulates deceleration of the vehicle as it deforms. Previous test methods do not employ a spring member, thus the test results do not correlate closely to full vehicle impact tests.

The data acquisition of the present method is superior to the data acquisition of the previous test methods. In the present method, the data may be captured by use of a sImple accelerometer 60 mounted on the mass element 42. The deceleration of the mass can easily be equated. to the relative forces acting on the column, given the mass element. The-prior testing methods utilize a 5-axis load cell with 5 channels to monitor the forces and moments on steering column 12. This data is collected as is known in the art and then combined to provide the overall force on the shaft.

Lastly, the present method provides improved camera coverage of the column during deformation. The present method, allows cameras to be mounted around the steering column assembly. Other testing methods, mainly impact testing do not allow cameras to be positioned around the steering column because of possible damage from the impact with the steering column assembly. It is also desirable that the steering column 12 be mounted upside down to show the collapse of the steering column components.

While the present invention has been described in the specification and illustrated in the drawings with reference to a preferred embodiment, it will be understood by those skilled in the art that various changes may be made and equivalents may be substituted for elements thereof without departing from the scope of the invention as defined in the claims. In addition, many modifications may be made to adapt a particular situation or material to the teachings of the invention without departing from the essential scope thereof. Therefore, it is intended that the invention not be limited to the particular embodiment illustrated by the drawings and described in the specification as the best mode presently contemplated for carrying out this invention, but that the invention will include any embodiments falling within the description of the appended claims.

What is claimed is:

1. An apparatus for testing the crash worthiness of an automobile steering column assembly, the steering column assembly having a column housing, a main shaft and an intermediate shaft in rotational communication with said main shaft, the apparatus comprising:

a mobile carrier unit, wherein said mobile carrier unit includes a spring member extending generally outward from an end thereof;

a fixture attached to said mobile carrier unit, said fixture including a mounting structure adapted for retaining the steering column assembly; and a mass element connected to the main shaft of said steering column assembly.

2. The apparatus of claim 1 further comprising a base unit, wherein said base unit is attached to the mobile carrier unit and adapted for retaining said fixture.

3. The apparatus of claim 2 wherein said fixture includes a first link for attaching said base unit to said fixture.

4. The apparatus of claim 3 wherein said fixture includes a second link for attaching said base unit to said fixture.

5. The apparatus of claim 4, wherein said first and second link contain a plurality of attachment points allowing said fixture to be positioned at different angles with respect to said mobile carrier unit.

6. The apparatus of claim 5, wherein said fixture further includes a blocker adapted to be adjacent to the intermediate shaft of the steering column.

7. The apparatus of claim 1, wherein said wherein said mobile carrier unit includes a plurality of wheels.

* * * * *